United States Patent [19]

Sohda et al.

[11] Patent Number: 5,240,950
[45] Date of Patent: Aug. 31, 1993

[54] CARBAZATE DERIVATIVES, THEIR PRODUCTION AND USE

[75] Inventors: Takashi Sohda, Takatsuki; Hitoshi Ikeda, Higashiosaka; Yu Momose, Neyagawa, all of Japan

[73] Assignee: Takeda Chemical Industries, Ltd., Osaka, Japan

[21] Appl. No.: 403,288

[22] Filed: Sep. 7, 1989

[30] Foreign Application Priority Data

Sep. 8, 1988 [JP] Japan .................. 63-225198
Jul. 4, 1989 [JP] Japan .................. 1-173369

[51] Int. Cl.$^5$ .................. C07D 277/42; A61K 43/78
[52] U.S. Cl. .................. 514/370; 514/272; 514/310; 514/313; 514/353; 514/361; 514/363; 514/367; 514/377; 514/380; 514/407; 544/332; 546/143; 546/163; 546/306; 548/128; 548/138; 548/161; 548/194; 548/233; 548/246; 548/375; 548/371.7
[58] Field of Search .......... 548/194, 233, 161, 138, 548/128, 246, 375; 544/332; 516/306, 143, 163; 514/370, 367, 377, 363, 361, 380, 407, 272, 353, 310, 313

[56] References Cited

PUBLICATIONS

Nagarajan, Ind. J. of Chem. 23B 342 (1984).
Bull. So. Chim. Fr., (1962) "Recherches sur les dérivés du triazole-1,2,4. III.-Emploi de l'hydrazinocarbonates d'éthylate pour la synthèse des hydroxy-3 triazoles-1,2,4" M. Pesson, pp. 1364–1371.
J. Chem. Soc. Perkin Trans. I (1987) "Ring Closure of ortho-Blocked 4-Aryl-1,2,3-triaze-1,3-dienes via 1,6--Electrocyclisation followed by Diels-Alder Dimerisation", R. Trave, pp. 1533–1536.

*Primary Examiner*—Robert Gerstl
*Attorney, Agent, or Firm*—Wegner, Cantor, Mueller & Player

[57] ABSTRACT

There are provided carbazate derivatives of the formula:

$$R^1-N=CH-NHNH-R^2$$

wherein $R^1$ is a heterocyclic group; and $R^2$ is an esterified carboxyl group, and their salts, which are useful as AGE-formation inhibitory agents.

The derivatives or the salts can be produced by reacting compounds of the formula: $R^1-N=CH-OR^3$ wherein $R^1$ is a heterocyclic group; and $R^3$ is a lower alkyl group, with a carbazic acid ester or its salt.

12 Claims, No Drawings

CARBAZATE DERIVATIVES, THEIR PRODUCTION AND USE

This invention relates to carbazic acid derivatives, or their salts, which exhibit inhibitory activity of AGE formation.

In recent years, an increased attention is attracted to the glycosylated products of proteins through the non-enzymatic glycosylation, which is considered to be responsible for a variety of pathogenesis related to diabetes and atherosclerosis. The nonenzymatic glycosylation involves the chemical attachment of blood glucose to protein amino groups to form a Schiff base, followed by Amadori rearrangement to relatively stable ketoamine derivatives (1-amino-1-deoxyfructose), which cause changes in the structure and function of proteins. The resultant Amadori rearrangement products slowly dehydrate and rearrange themselves in several months to several years, and form irreversible advanced glycosylation end products (AGE). AGE are yellowish brown and fluorescent, and easily bind with adjacent proteins to form crosslinks. The proteins, which have formed crosslinks through AGE formation, are thought to cause disturbances in various tissues. In diabetes, the nonenzymatic glycosylation of proteins increases in proportion to blood glucose levels, and this is regarded as one of the causes for diabetic complications [A. Cerami et al., "Metabolism" 28 (Suppl. 1) 431 (1979): V. M. Monnier et al., "The New England Journal of Medicine", 314, 403 (1986)]. The process is also considered to be responsible for aging. Senile cataract involves the AGE formation of a protein existing in the crystalline lens of the eye. Furthermore, pathologic changes of atherosclerosis are associated with the AGE formation, as well. It has been confirmed that AGE are involved in the thickening of capillary basement membrane associated with aging and the thickening of glomerular basement membrane being responsible for renal insufficiency or failure [M. Brownlee et al. "Science", 232, 1629 (1986)].

M. Brownlee et al reported that aminoguanidine can prevent the transformation of Amadori rearrangement products into AGE [M. Brownlee et al. "Science", 232, 1629 (1986)] and the compound is noted as a candidate for Prevention of diseases associated with aging.

In order to prevent and treat the diseases caused by AGE formation, there are called for the inhibitors of AGE formation. Since aminoguanidine, as reported previously, has no adequate inhibitory activity, a more potent inhibitor of AGE formation is expected to be developed.

The present inventors, after extensive and intensive research on compounds being useful for the prevention of the above-mentioned diseases through inhibition of AGE formation, found that novel carbazic acid derivatives, represented by the formula:

$$R^1—N=CH—NHNH—R^2 \quad (I)$$

wherein $R^1$ is a heterocyclic group and $R^2$ is an esterified carboxyl group, or their salts, are obtained by reacting a compound represented by the formula:

$$R^1—N=CH—OR^3 \quad (II)$$

wherein $R^1$ is as defined in the above and $R^3$ is a lower alkyl group with a carbazate or its salt, and that the carbazic acid derivatives, represented by the formula:

$$R—N=CH—NHNH—R^2 \quad (III)$$

wherein R is a heterocyclic or aryl group and $R^2$ is as defined in the above, or their salts, inclusive of the thus-obtained carbazic acid derivatives (I) or their salts, possess excellent inhibitory activity of AGE formation, and the findings have culminated into the present invention.

Referring to the above-described formulae, the heterocyclic group represented by $R^1$ and R includes heterocyclic groups having a linkage on a ring-constituting carbon atom, preferably 5-membered or 6-membered unsaturated heterocyclic rings containing 1 to 4 of nitrogen, oxygen sulfur, etc. as a ring constituting heteroatom or their condensed ring groups. Such heterocyclic groups show normally a molecular weight of 60 to 300, preferably 60 to 200. Specific examples of these heterocyclic groups as used include 2-, 3- or 4-pyridyl, 2-or 3-thienyl, 2- or 3-furyl, 2-, 4- or 8-quinolyl, 1-, 4- or 8-isoquinolyl, 2-, 4- or 5-pyrimidinyl, 3- or 4-pyridazinyl, 2-, 4- or 5-thiazolyl, 2-, 4- or 5-oxazolyl, 3-, 4- or 5-isoxazolyl, 3-, 4- or 5-pyrazolyl, 2-, 4- or 5-imidazolyl, 4- or 5-(1,2,3-oxadiazolyl), 3- or 5-(1,2,4-oxadiazolyl), 1,3,4-oxadiazolyl, 1,2,5-oxadiazolyl, 3- or 5-(1,2,4-thiadiazolyl), 1,3,4-thiadiazolyl, benzimidazolyl, benzothiazolyl, tetrahydrobenzthiazolyl, quinolyl, quinazolyl, pteridinyl or benzoxazolyl groups. In addition, the heterocyclic group represented by $R^1$ and R include those having 1 to 4 of the same or different substituents on the ring, and such substituents may be chosen for example from those as described in the following (i) to (x). (i) Aromatic groups, such as $C_{6-14}$ aryl being exemplified by phenyl, naphtyl, tetrahydronaphthyl and anthryl, which may be substituted for example by 1 to 4 of alkyl groups, halogens and hydroxyl, nitro, acyl, acylamino, aminoalkylthio and aralkylthio groups.

With reference to the above, preferably used as the alkyl group are, for example, $C_1$ to $C_{10}$ straight-chain, branched or cyclic alkyl groups which may be substituted in arbitrary positions by 1 to 4 of halogen atoms (Br, Cl, I; etc.), and there are used, for example, methyl, trifluoromethyl, ethyl, 2,2,2-trifluoroethyl, 2,2,2-trichloroethyl, propyl, isopropyl, butyl, isobutyl, sec-butyl, tert-butyl, cyclobutyl, pentyl, isopentyl, neopentyl, cyclopentyl, hexyl, cyclohexyl, heptyl, cycloheptyl, 2-methylcyclohexyl, octyl, nonyl, decyl, etc.

As examples of the halogen, there are used fluorine, chlorine, bromine and iodine, with chlorine being among others preferable.

As the hydroxyl group, there may be mentioned hydroxyl group and those having a suitable substituent, particularly those used as a protective group for hydroxyl, in the hydroxyl group, such as alkoxy (for example, alkoxy having a number of carbon atoms of 1 to 8, being specifically exemplified by methoxy, ethoxy, propoxy, isopropoxy, butoxy, isobutoxy, sec-butoxy, tert-butoxy, pentoxy, neopentoxy, hexyloxy,

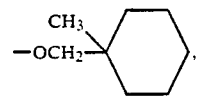

etc.), aralkyloxy (for example, phenyl-$C_{1-4}$ alkyloxy which may be substituted by 1 to 4 of halogens (Cl, Br, I, etc.), being specifically exemplified by benzyloxy, phenethyloxy, p-chlorobenzyloxy, etc.), acyloxy (for example, $C_2$ to $C_4$ alkanoyloxy, being specifically exemplified by acetyloxy, propionyloxy, n-butyryloxy, isobutyryloxy, etc.), aryloxy (for example, $C_6$ to $C_{10}$ aryloxy which may be substituted by 1 to 4 of halogens (Cl, Br, I, etc.), being specifically exemplified by phenoxy, p-chlorophenoxy, etc.) and the like.

As the acyl group, there may be used, for example, acyl groups consisting of $C_1$ to $C_{10}$ alkyl bonded to carbonyl (for example, acetyl, propionyl, butyryl, isobutyryl, valeryl, isovaleryl, pivaloyl, hexanoyl, heptanoyl, octanoyl, nonanoyl, etc.), acyl groups consisting of $C_6$ to $C_{10}$ aryl, which may be substituted by 1 to 4 of halogens (Cl, Br, I, etc.) or $C_1$ to $C_4$ alkoxy (methoxy, ethoxy, etc.), being attached to carbonyl (for example, benzoyl, p-chlorobenzoyl, p-methoxybenzoyl, naphthoyl, etc.) and the like.

As the acylamino group, there are used, for example, acylamino groups consisting of the acyl groups, which are exemplified above as the acyl group, being attached to amino groups.

As the amino group, there may be mentioned amino group and those substituted by 1 or 2 of $C_{1-10}$ alkyl groups, $C_{7-12}$ aralkyl groups and sulfonyl groups (for example, methylamino, ethylamino, propylamino, butylamino, pentylamino, cyclohexylamino, dimethylamino, dibutylamino, dihexylamino, benzylamino, N-benzyl-N-methylamino, N-(4-chlorobenzyl) N-tosylamino, sulfonylamino, etc.) and the like.

As the alkylthio or aralkylthio group, there may be mentioned, for example, groups consisting of the abovedescribed alkyl or $C_7$ to $C_{12}$ aralkyl (benzyl, phenylethyl, etc.) groups bonded to a sulfur atom, which may be substituted by 1 to 4 of halogens (Cl, Br, I, etc.), and specifically, there are used methylthio, ethylthio, propylthio, butylthio, benzylthio, p-chlorobenzylthio, phenethylthio, etc.

(ii) Heterocyclic groups, such as 5-membered of 6-membered saturated or unsaturated heterocyclic groups containing at lest one of heteroatoms, e.g. nitrogen oxygen and sulfur atoms, or their condensed heterocyclic groups (heteropolycyclic groups) (for example, pyrrolyl, imidazolyl, pyrazolyl, pyridyl, pyrimidyl, tetrazolyl, oxazolyl, isoxazolyl, oxadiazolyl, morpholino, thiazolyl, isothiazolyl, benzoxazolyl, benzofuryl, benzothienyl, etc.), which may be substituted for example by 1 to 4 of alkyl groups, halogens, and hydroxyl, nitro, acyl, acylamino, amino, alkylthio and aralkylthio groups as mentioned above in the item (i).

(iii) Alkyl groups, such as those as mentioned above in the item (i), are used.

(iv) Halogens, such as those as described above in the item (i), are employed.

(v) Hydroxyl group, such as those as mentioned above in the item (i), are used.

(vi) Nitro group.

(vii) Acyl groups, such as those as mentioned above in the item (i), are used.

(viii) Acylamino groups, such as those as described above in the item (i), are employed (ix) Amino groups, such as those as mentioned above in the item (i), are used.

(x) Alkylthio groups, such as those as mentioned above in the item (i), are used.

(xi) Aralkylthio groups, such as those as mentioned above in the item (i), are used.

Preferred examples of the heterocyclic group is represented by $R^1$ and R include thiazolyl groups which may be substituted for example by 1 to 2 of lower alkyl groups (for example, $C_1$ to $C_4$ alkyl groups such as methyl, ethyl, propyl, n-butyl and i-butyl), $C_6$ to $C_{10}$ aryl groups (for example, phenyl, naphthyl and the like, which may be substituted by for example $C_3$ to $C_6$ cycloalkyl groups such as cyclopropyl, cyclobutyl, cyclopentyl and cyclohexyl or phenyl-$C_{1-3}$ alkyloxy groups which may be substituted by 1 to 4 of halogens such as benzyloxy and 4-chlorobenzyloxy) and others.

Referring now to the above-described formula (III), the aryl group represented by R includes, for example, $C_6$ to $C_{10}$ aryl groups, such as phenyl and naphtyl, which may be substituted by 1 to 4 of the substituents (i) to (xi) as mentioned above for the heterocyclic groups represented by $R^1$ and R. As the preferable examples of the aryl group represented by R, there may be used phenyl groups which may be substituted for example by 1 to 2 of halogens (Cl, Br, I, etc.), $C_1$ to $C_4$ alkoxy groups (methoxy, ethoxy, etc.) and halogeno-$C_1$ to $C_4$ alkyl groups (chloromethyl, dichloroethyl, trifluoromethyl, etc.), and the like.

In the above formulae (I) and (III), $R^2$ represents an esterified carboxyl group, and includes for example groups of the formula $-COOR^{2a}$ or $-COSR^{2a}$ (wherein $R^{2a}$ is an ester residue). As the ester residue represented by $R^{2a}$, there are used for example $C_1$ to $C_{10}$ alkyl, $C_6$ to $C_{14}$ aryl and phenyl-$C_1$ to $C_4$ alkyl groups, as mentioned above for the substituents in the heterocyclic groups represented by R1 and R, which may be substituted by 1 to 3 of halogens (Cl, Br, F, etc.), $C_1$ to $C_4$ alkoxy (methoxy, ethoxy, propoxy, t-butoxy, n-butoxy, i-butoxy, etc.) and the like. Specific examples of the ester residue represented by $R^{2a}$ include $C_1$ to $C_8$ alkyl groups, such as methyl, ethyl, propyl, isopropyl, n-butyl, isobutyl, tert-butyl, sec-butyl, cyclobutyl, pentyl, isopentyl, neopentyl, cyclopentyl, hexyl, cyclohexyl, heptyl, cyclohexylmethyl, cycloheptyl, 2-cyclohexylethyl and octyl, $C_6$ to $C_{14}$ aryl groups which may be substituted by a halogen or $C_{1-4}$ alkoxy such as phenyl, 4-chlorophenyl, 4-methoxyphenyl, 2-chlorophenyl and naphthyl and phenyl-$C_1$ to $C_4$ alkyl groups which may be substituted by 1 or 2 of the halogens or $C_{1-4}$ alkoxy groups, such as benzyl, phenetyl, 4-chlorobenzyl, 3,4-dimethoxyphenethyl and 3-(3-trifluorophenyl)propyl. Preferred examples of the ester residue represented by $R^{2a}$ include $C_1$ to $C_4$ alkyl groups, such as methyl, ethyl, propyl, n-butyl and t-butyl, and $C_6$ to $C_{10}$ aryl group, such as phenyl.

As the lower alkyl group represented by $R^3$ in the above formula (II), there are used preferably $C_1$ to $C_4$ alkyl groups such as methyl, ethyl, propyl, isopropyl, n-butyl, i-butyl and t-butyl, and others.

Preferred examples of the novel carbazic acid derivatives (I) or their salts according to this invention include compounds represented by the formula:

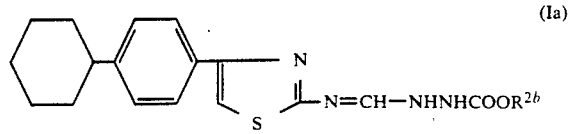

(Ia)

wherein $R^{2b}$ is a $C_1$ to $C_4$ alkyl group, such as methyl, ethyl, propyl, n-butyl and t-butyl, or a $C_6$ to $C_{10}$ aryl group, such as phenyl, or their salts and compounds represented by the formula:

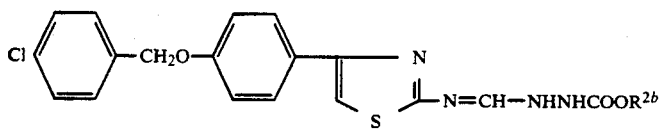

(Ib)

wherein $R^{2b}$ is as defined above, or their salts.

The carbazic acid derivatives (I) and (III) can also be used in the form of salts, such as pharmaceutically acceptable salts to be produced with use of suitable acids by means of the conventional procedures. As the above acid salts, there are used, for example, mineral acid salts (hydrochloride, hydrobromide, sulfate, etc.), organic acid salts (succinate, maleate, fumarate, citrate, tartrate etc.), sulfonates (methanesulfonate, benzensulfonate, toluensulfonate, etc.) and the like, and these salts can all be produced by the known means.

The carbazic acid derivatives (I) and (III) are considered to be in equilibrium with their respective tautomers (I') and (III') of the following formulae:

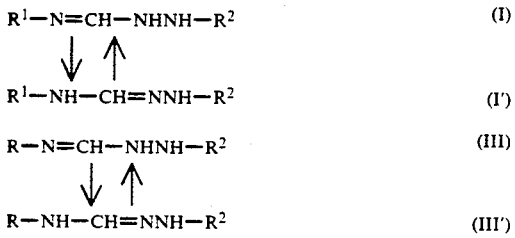

In this specification, (I') and (III') are understood to be included in (I) and (III), respectively, and are named in accordance with the formulae (I) and (III). Furthermore, the compounds (I) or (I') and (III) or (III') produce cis and trans isomers in terms of the double bond —N=CH— or —CH=N—, and these individual isomers and mixtures thereof are all included in the compounds (I) and (III), respectively.

The compounds (I) of this invention can be produced, for example, by the following procedure.

Thus, the compounds (I) or their salts can be produced by reacting a compound represented by the formula:

wherein the symbols are as defined in the above with a carbazic acid ester represented by the formula:

wherein $R^2$ is as defined in the above, or its salt (for example, the salts as mentioned above for the salts of the carbazic acid derivatives (I) and (III)).

In this reaction, the compounds (II) and (III) can be allowed to undergo an equimolar reaction, but either of these compounds may be used in slight excess. Also, the reaction may be carried out in a suitable solvent. As the solvent, there are used for example alcohols, such as methanol, ethanol, 2-propanol, butanol and 2-methoxyethanol, ethers, such as dioxane, tetrahydrofuran and dimethoxyethane, aromatic hydrocarbons, such as benzene, toluene and xylene, and halogenated hydrocarbons, such as chloroform, dichloromethane, 1,2-dichloroethane and 1,1,2,2-tetrachloroethane, or solvent mixtures thereof. The volume of the solvent used is not specifically limited, unless it affects adversely the reaction, but is normally in the proportion of 0.1 to 10 liters to 1 mole of the compound (II), preferably 0.5 to 5 liters. The reaction temperature is normally in the range of −20° C. to 100° C., preferably about 0° C. to 80° C. The reaction time ranges normally from 10 minutes to 50 hours, preferably from 0.5 to 10 hours. The carbazic acid derivative (I), or its salt, as obtained in the above manner can be isolated and purified by the known separation and purification procedures, such as concentration, concentration under reduced pressure, solvent extraction, crystallization, recrystallization, phase inversion dissolution and chromatography. When the compound (I) or its salt consists of a mixture of isomers, they can also be separated in accordance with the conventional method.

The starting compound (II) to be used in this invention can be produced for example by the following procedure, as well.

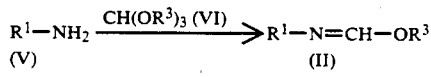

wherein $R^1$ and $R^3$ are as defined in the above.

In this procedure, the amine derivative (V) is reacted with the ortho-ester (VI) to produce (II). This reaction may be carried out by heating (v) and (VI) in the presence or absence of a suitable solvent. As the said solvent, there are used for example ethers, such as dioxane, tetrahydrofuran and dimethoxyethane, aromatic hydrocarbons, such as benzene, toluene and xylene, ethyl acetate, acetonitrile, pyridine, N,N-dimethylformamide, dimethylsulfoxide, chloroform, dichloromethane, 1,2-dichloroethane, 1,1,2,2,-tetrachloroethane or solvent mixtures thereof. The reaction temperature ranges normally from about 10° C. about 200° C., preferably from about 20° C. to about 150° C., while the reaction time is normally in the range of 10 minutes to 50 hours, preferably about 0.5 to 10 hours. The compound (II) obtained in this manner can be used as a starting material in this invention after being separated by the above-described known procedure, but can also be utilized as the reaction mixture and without being separated, as a starting material in this invention The amine derivative (V) as used in the above procedure for the production of the compound (II) can be produced by the methods, or method similar thereto, as described in Chemical Abstracts, 53, 14089e (1959); Chemical Abstracts, 105, 221003s (1986); European Journal of Medicinal Chemistry, 16, 335 (1981); *Shin-Jikken Kagaku Koza* (New Discourse on Experimental Chemistry), 14, "Syntheses and Reactions of Organic Compounds [IV]" (1976) and others, while the ortho-ester (VI) can be prepared for example by the method, or methods similar thereto, as described in *Shin-Zikken*

*Kagaku Koza* (New Discourse on Experimental Chemistry), 14, "Syntheses and Reactions of Organic Compounds [IV]" (1976).

The carbazic acid ester or its salt, which is the ether starting compound (IV) in the procedure of this invention, can be produced by the known method, or methods similar thereto, as described for example in Journal of Organic Chemistry, 37, 2413 (1972).

The carbazic acid derivatives (III) and their salts, because of their excellent AGE-formation inhibitory activities, can find application as drugs for human beings and livestock, and are usable safely as an AGE-formation inhibitory agent that acts to treat, cure and prevent a variety of diseases caused by the transformation of proteins into AGE.

The carbazic acid derivatives (III) or their salts can be processed solely or in combination with other active ingredients and after being incorporated with adjuvants, such as neutralizing agent, stabilizer and dispersant, if necessary, in accordance with the conventional procedure, and used in the forms of dosage preparations, such as capsules, tablets, powders, solutions suspensions or elixirs. These preparations can be administered parenterally (for example, through rectal administration) or orally.

The carbazic acid derivatives (III) or their salts are admixed, as the case may be, with binders, such as syrup, gum arabic, gelatin, sorbitol, gum tragacanth and polyvinylpyrrolidone, fillers, such as lactose, sugars, corn starch, calcium phosphate, sorbitol and glycine, lubricants, such as magnesium stearate, talc, polyethylene glycol and silica, disintegrating agents, such as potato starch or wetting agents, such as sodium lauryl sulfate, and then can be processed into pharmaceutical preparations for oral administration, such as tablets, capsules, granules and powders, in accordance with the conventional methods. Tablets, granules, etc. can be subjected to film coating by the procedures known per se, as well. Pharmaceutical preparations for oral administration may be employed in the forms of liquid preparations, such as aqueous or oil-borne suspensions, solutions, emulsions and elixirs.

Pharmaceutical preparations for rectal administration containing the carbazic acid derivatives (III) or their salts are produced in accordance with the conventional method by mixing a suppository base and additives with the carbazic acid (III) or its salts and then forming the mixture for example into oily solid suppositories, semi-solid ointment-like suppositories and capsule suppositories having a liquid composition filled into soft capsules. The carbazic acid derivative (III) or its salt is formulated normally at a ratio chosen from the range of about 0.5 to 50 weight %, but the formulation proportion is in no way limited to the range. In this invention, other non-ionic surfactants, such as polyoxyethylene fatty acid esters and polyoxyethylene higher alcohol ethers, may be added simultaneously to the preparations or anionic surfactants can also be formulated for the purpose of enhancing the bioavailability of the carbazic acid derivative (III) or its salt or for the purpose of controlling its absorption rate. In addition, there can be formulated or added a variety of salts or stabilizers in order to increase solubility or stability of the carbazic acid derivative (III) or its salt. Further, dispersing agents, preservatives, etc. can also be added, if necessary from the standpoint of pharmaceutical processing.

Also, other ingredients, such as known antioxidants, preservatives, lubricants, viscosity-increasing agents of flavors, may be admixed into these pharmaceutical preparations in accordance with the conventional methods. Furthermore, other active ingredients can also be incorporated into the pharmaceutical preparations to produce the preparations which can exhibit desired inhibitory activity of AGE formation.

The carbazic acid derivatives (III) or their salts can be used as an AGE-formation inhibitory agent, for example, in the treatment and prevention of diabetic complications, senile cataracts, atherosclerosis, glomerular basement membrane thickening, etc. in the human being and other mamalians. The daily dose of the carbazic acid derivatives (III) or their salts vary depending upon the conditions and body weight of patients, the route of administration and the like, but the compounds are administered parenterally to human adults in the daily dose of about 0.05 to 80 mg as an active ingredient (the carbazic acid derivative (III) or its salt) per kg body weight, preferably about 0.1 to 10 mg, and are suitably given through rectal administration as divided into twice to four times a day. The compounds are suitably administered orally to adults in the dose of about 0.5 to 100 mg as an active ingredient (the carbazic acid derivative (III) or its salt) per kg body weight as divided into once to three times a day.

It is to be further added that the carbazic acid derivative (III) or its salts allow excellent distribution within the body and are substantially free from side-effects, thereby constituting the ideal AGE-formation inhibitory agent that can demonstrate the therapeutic and preventive effects against diseases brought about by the transformation of proteins into AGE.

EXPERIMENT EXAMPLE

The production and measurement of advanced glycosylation end products (AGE) were carried out according to the method of M. Brownlee et al. [Science, 232, 1629 (1986)]. Namely, Bovine serum albumin (fraction V, manufactured by Wako Pure Chemical of Japan, 20 %), D-glucose (100 mM) and sodium azide (3 mM) were dissolved in 0.5 M-phosphate buffer solution (pH 7.4) to prepare a reaction solution (control). Test compounds (the compounds as obtained in the below-described examples), after being dissolved in dimethylsulfoxide, were added to the reaction solution at a concentration of 1 mM, respectively. These solutions were incubated at 37° C. for 7 days. Before and after incubation, the solutions were diluted with phosphate buffer to measure fluorescence at the excitation and emission wavelengths of 370 nm 440 nm, respectively, using a spectrofluorimeter (Model RF-510 of Shimazu Seisakusho). Changes ($\Delta F$) in fluorescence were used to calculate the AGE production ratios (%) by the following equation, whereby the reaction solution without D-glucose contained was used as a blank. The results are shown in Table 1.

*AGE production*
$$ratio = [\Delta F(t) - \Delta F(b) / \Delta F(c) - \Delta F(b)] \times 100$$

Where ; $\Delta F(t)$ is $\Delta F$ found for test compounds,
$\Delta F(b)$ is $\Delta F$ found for blind test
$\Delta F(c)$ is $\Delta F$ found for control.

TABLE 1

| Compound in Example No. | AGE production ratio (% against control value) |
| --- | --- |
| 1 | 66 |
| 2 | 64 |
| 3 | 59 |
| 4 | 22 |
| 5 | 47 |
| 9 | 46 |
| 10 | 43 |
| 11 | 61 |
| 14 | 56 |
| 17 | 66 |
| 26 | 54 |
| 27 | 45 |
| 28 | 63 |
| 31 | 66 |
| 33 | 47 |
| 34 | 41 |
| 41 | 0 |

Table 1 reveals that AGE formed after addition of the carbazic acid derivatives (III) or their salts to the reaction solution was extremely lower than found without addition of the same (AGE formation ratio was taken as 100 %), and consequently demonstrates clearly that the carbazic acid derivatives (III) or their salts possess excellent AGE-formation inhibitory activity.

Since the carbazic acid derivatives (III) or their salts exhibit excellent AGE-formation inhibitory activity, this invention can provide novel AGE-formation inhibitory agents that are useful for the prevention and treatment of diseases being brought about by the glycosylated proteins into AGE.

The reference example and examples are described in the following to illustrate this invention more specifically. The melting points (mp) to be given throughout the examples are as determined by the hot plate method and not corrected.

REFERENCE EXAMPLE 1

A mixture of 2-amino-4-(4-cyclohexylphenyl)thiazole hydrochloride (1.0 g) and triethyl orthoformate (5 ml) was stirred at 130° C. for 1 hour. The reaction mixture was concentrated under reduced pressure, and to the remaining crystals was added hexane, followed by filtration. The filtrate was concentrated to give crystals of 4-(4-cyclohexylphenyl)-2-ethoxymethyleneaminothiazole (1.02 g, yield of 95.6 %). Recrystallization from diethyl etherhexane produced yellowish prisms, mp of 84° to 85° C.

Elemental analysis, for $C_{18}H_{22}N_2OS$ Calcd.: C, 68.76; H, 7.05; N, 8.91; Found : C, 68.73; H, 7.06; N, 8.93.

EXAMPLE 1

A mixture consisting of 4-(4-cyclohexylphenyl)-2-ethoxymethyleneaminothiazole (500 mg), ethyl carbazate (170 mg) and ethanol (10 ml) was stirred under ice-cooling for 1 hour and then at room temperature (about 15° C.) for 18 hours. The reaction mixture was concentrated under reduced pressure, and the crystals were collected by filtration with hexane to give ethyl 3-[4-(4-cyclohexylphenyl)-2-thiazolyliminomethyl]carbazate (515 mg, yield of 87 %). Recrystallization from dimethylforamide-water produced colorless prisms, mp of 188 to 189° C.

Elemental analysis, for $C_{19}H_{24}N_4O_2S$: Cald.: C, 61.27; H, 6.49; N, 15.04. Found : C, 61.32; H, 6.52; N, 14.97.

EXAMPLE 2

A mixture of 2-amino-4-(5,6,7,8-tetrahydro-2-naphthyl) thiazole (1.5 g) and ethyl orthoformate (30 ml) was stirred at 130 to 135° C. for 2 hours and concentrated under reduced pressure. The residue was dissolved in ethanol (20 ml), and the solution was admixed with ethyl carbazate (680 mg), followed by stirring at room temperature (about 15° C.) for 6 hours. The solvent was evaporated off, and the remaining crystals were collected by filtration with diisopropyl ether to give ethyl 3-[4-(5,6,7,8-tetrahydro-2-naphthyl)-2-thiazolyliminomethyl]carbazate (1.84 g, yield of 82 %). Recrystallization from ethanol produced colorless prisms, mp of 134° to 135° C.

Elemental analysis, for $C_{17}H_{20}N_4O_2S$: Calcd. : C, 59.28; H, 5.85; N, 16.29; Found : C, 59.61; H, 5.91; N, 16.05.

EXAMPLES 3 THROUGH 42

By following the same procedure as described in Example 2, there were obtained the compounds as shown in Table 2.

TABLE 2

| Example No. | R—N=CH—NHNH—COOR$^{2a}$ R | R$^{2a}$ | Yield % | Recrystallization solvent | mp °C. |
| --- | --- | --- | --- | --- | --- |
| 3 | cyclohexyl-phenyl-thiazolyl | CH$_3$ | 85.1 | DMF—H$_2$O | 194–195 |
| 4 | cyclohexyl-phenyl-thiazolyl | tert-C$_4$H$_9$ | 87.8 | DMF—H$_2$O | 203–204 |
| 5 | cyclohexyl-phenyl-thiazolyl | phenyl | 65.4 | DMF—H$_2$O | 210–212 |

TABLE 2-continued

| Example No. | R—N=CH—NHNH—COOR$^{2a}$ R | R$^{2a}$ | Yield % | Recrystallization solvent | mp °C. |
|---|---|---|---|---|---|
| 6 | 4-cyclohexylphenyl, α-methyl-thiazolyl derivative | C$_2$H$_5$ | 57.1 | CH$_2$Cl$_2$—EtOH | 196–197 |
| 7 | 4-Cl-phenyl thiazolyl derivative | C$_2$H$_5$ | 74.7 | DMF—H$_2$O | 196–197 |
| 8 | 4-CF$_3$-phenyl thiazolyl derivative | C$_2$H$_5$ | 88.6 | DMF—H$_2$O | 198–199 |
| 9 | 3,4-dimethoxyphenyl thiazolyl derivative | C$_2$H$_5$ | 70.8 | EtOH—Et$_2$O | 136–137 |
| 10 | 4-chlorobenzyloxyphenyl thiazolyl derivative | C$_2$H$_5$ | 57.1 | CHCl$_3$—EtOH | 212–213 |
| 11 | 4-chlorobenzyloxyphenyl α-methyl-thiazolyl derivative | C$_2$H$_5$ | 82.8 | CH$_2$Cl$_2$—EtOH | 199–200 |
| 12 | 4-(neopentyloxy)phenyl thiazolyl derivative, (CH$_3$)$_3$CCH$_2$O— | C$_2$H$_5$ | 81.8 | CH$_2$Cl$_2$-i-Pr$_2$O | 165–166 |
| 13 | 4-(4-chlorobenzylthio)phenyl thiazolyl derivative | C$_2$H$_5$ | 90.8 | CH$_2$Cl$_2$—EtOH | 200–201 |
| 14 | 4-methylthiazolyl derivative | C$_2$H$_5$ | 68.0 | CH$_2$Cl$_2$—EtOH | 182–183 |
| 15 | cyclohexylmethyl thiazolyl derivative | C$_2$H$_5$ | 76.4 | CH$_2$Cl$_2$—EtOH | 189–190 |
| 16 | 5-nitrobenzothiazolyl derivative, O$_2$N— | C$_2$H$_5$ | 58.7 | CHCl$_3$—MeOH | 211–212 |

TABLE 2-continued

| Example No. | R—N=CH—NHNH—COOR[2a] R | R[2a] | Yield % | Recrystallization solvent | mp °C. |
|---|---|---|---|---|---|
| 17 | 4,5-dimethoxybenzo[d]thiazol-2-yl | $C_2H_5$ | 37.7 | $CH_2Cl_2$—EtOH | 185–186 |
| 18 | 2-(4-(4-chlorophenoxy)phenyl)thiazol-4-yl | tert-$C_4H_9$ | 67.1 | $CH_2Cl_2$—EtOH | 173–174 |
| 19 | 2-(3,4-dimethoxyphenyl)thiazol-4-yl | tert-$C_4H_9$ | 80.9 | $CH_2Cl_2$—EtOH | 187–188 |
| 20 | 2-(4-(4-chlorobenzoyl)phenyl)thiazol-4-yl | tert-$C_4H_9$ | 79.4 | $CH_2Cl_2$—EtOH | 213–214 |
| 21 | 2-(4-cyclohexylphenyl)-5-methyloxazol-4-yl | $C_2H_5$ | 69.9 | — | oil[1)] |
| 22 | 2-(4-chlorophenyl)oxazol-4-yl | $C_2H_5$ | 73.0 | $Me_2CO$-$iPr_2O$ | 146–147 |
| 23 | 2-(4-((1-methylcyclohexyl)methoxy)phenyl)oxazol-4-yl | $C_2H_5$ | 47.5 | $CH_2Cl_2$-$iPr_2O$ | 142–143 |
| 24 | 2,5-dimethyl-1,3,4-thiadiazole | $C_2H_5$ | 40.3 | DMSO—$H_2O$ | 207–208 |
| 25 | 3-phenyl-1,2,4-thiadiazol-5-yl | $C_2H_5$ | 80.1 | $CHCl_3$—EtOH | 215–216 |
| 26 | 3-methylisoxazol-5-yl | $C_2H_5$ | 61.9 | $CH_2Cl_2$—EtOH | 159–160 |
| 27 | 3,5-dimethyl-1-(4-methylphenyl)pyrazol-4-yl | $C_2H_5$ | 64.4 | $CH_2Cl_2$-hexane | 103–104 |

TABLE 2-continued

| Example No. | R—N=CH—NHNH—COOR[2a] R | R[2a] | Yield % | Recrystallization solvent | mp °C. |
|---|---|---|---|---|---|
| 28 | 2-pyrazinyl | C₂H₅ | 31.4 | CH₂Cl₂—EtOH | 184–185 |
| 29 | 3-methyl-6-pyridyl (5-methyl-2-pyridyl) | C₂H₅ | 41.2 | Me₂CO-iPr₂O | 153–154 |
| 30 | 1-isoquinolinyl | C₂H₅ | 68.1 | CH₂Cl₂—EtOH | 180–181 |
| 31 | 2-methyl-5,6,7,8-tetrahydroquinolinyl | C₂H₅ | 56.9 | CH₂Cl₂—EtOH | 200–201 |
| 32 | 2-chloro-4-trifluoromethylphenyl | C₂H₅ | 71.4 | CHCl₃-iPr₂O | 167–168 |
| 33 | 4-chlorophenyl | C₂H₅ | 67.0 | EtOH—H₂O | 167–168 |
| 34 | 4-methoxyphenyl | C₂H₅ | 84.4 | CH₂Cl₂-iPr₂O | 131–132 |
| 35 | 2-thiazolyl | C₂H₅ | 67.2 | CH₂Cl₂-iPr₂O | 112–114 |
| 36 | 4-(benzyloxy)phenyl-thiazolyl | C₂H₅ | 75.5 | CH₂Cl₂—EtOH | 187–188 |
| 37 | 4-phenyl-thiazolyl | C₂H₅ | 85.3 | CH₂Cl₂—EtOH | 183–184 |
| 38 | tetrahydronaphthyl-thiazolyl | tert-C₄H₉ | 68.0 | CH₂Cl₂—EtOH | 192–193 |
| 39 | 3-methyl-isoxazolyl | tert-C₄H₉ | 65.7 | CH₂Cl₂—EtOH | 184–185 |

TABLE 2-continued

| Example No. | R—N=CH—NHNH—COOR$^{2a}$ R | R$^{2a}$ | Yield % | Recrystallization solvent | mp °C. |
|---|---|---|---|---|---|
| 40 | 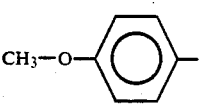 | tert-C$_4$H$_9$ | 53.1 | CH$_2$Cl$_2$-iPr$_2$O | 143–144 |
| 41 | 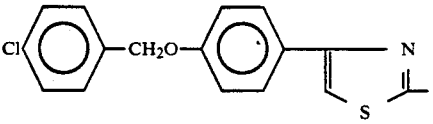 | tert-C$_4$H$_9$ | 91.4 | CH$_2$Cl$_2$—EtOH | 219–221 |
| 42 | 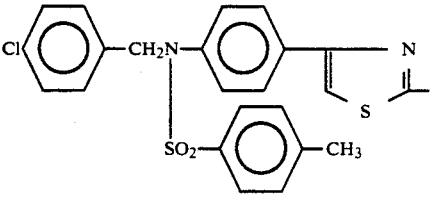 | C$_2$H$_5$ | 88.1 | — | oil$^{2)}$ |

1) NMR (δppm in CDCl$_3$: 1.28(3H, t, J=7 Hz), 1.0–2.1(10H,m), 2.3–2.7(4H, m), 4.28(2H, q, J=7 Hz), 7.5–7.6(6H, m)

2) NMR (δppm in d$_6$.DMSO): 1.21 (3H, t, J=7 Hz), 2.41(3H, s), 4.09(2H, q, J=7Hz), 4.78(2H, broad s), 7.05(2H, d, J=8.5 Hz), 7.25–7.8(11H, m), 8.09(1H, broad s), 10.25(1H, broad s), 10.76 (1H, broad s).

In the above Table, "DMF", "DMSO", "EtOH", "i-Pr$_2$O", "MeOH" and "Me$_2$CO" stand for dimethylformamide, dimethylsulfoxide, diisopropyl ether, methanol and acetone, respectively.

What is claimed is:

1. A carbazic acid derivative of the formula $$R^1-N=CH-NHNH-R^2$$

wherein R$^1$ is a 2-, 3- or 4-pyridyl, 2- or 3-thienyl, 2- or 3-furyl, 2-, 4- or 8-quinolyl, 1-, 4- or 8-isoquinolyl, 2-, 4- or 5-pyrimidinyl, 3- or 4-pyridazinyl, 2-, 4- or 5-thiazolyl, 2-, 4-or 5-oxazolyl, 2-, 4- or 5-isoxazolyl, 3-, 4- or 5-pyrazolyl, 4-or 5-(1,2,3-oxadiazolyl), 3- or 5(1,2,4-oxadiazolyl), 1,3,4-oxadiazolyl, 1,2,5-oxadiazolyl, 3- or 5(1,2,4-thiadiazolyl), 1,3,4-thiadiazolyl, benzimidazolyl, benzothiazolyl, tetrahydrobenzothiazolyl, quinazolyl, pteridinyl or benzoxazolyl group which may be substituted with 1 to 4 of the same or different substituents chosen from (i) a C$_{6-14}$ aryl which may be substituted by 1 to 4 of
 (a) C$_{1-10}$ straight-chain, branched or cyclic alkyl group which may be substituted by 1 to 4 halogen atoms,
 (b) halogen,
 (c) hydroxyl, C$_{1-4}$ alkoxy, phenyl-C$_{1-4}$ alkyloxy which may be substituted by 1 to 4 of halogen atoms, C$_{2-4}$ alkanoyloxy, or C$_{4-10}$ aryloxy which may be substituted by 1 to 4 halogen atoms,
 (d) nitro,
 (e) C$_{1-10}$ alkylcarbonyl, or C$_{6-10}$ arylcarbonyl wherein the aryl group may be substituted by 1 to 4 of halogen atoms or C$_{1-4}$ alkoxy,
 (f) acylamino wherein the acyl group is a C$_{1-10}$ alkylcarbonyl or C$_{6-10}$ arylcarbonyl wherein the aryl group may be substituted by 1 to 4 halogen atoms or C$_{1-4}$ alkoxy,
 (g) amino which may be substituted by 1 to 4 of C$_{1-10}$ alkyl, C$_{7-10}$ aralkyl and sulfonyl groups, or
 (h) C$_{1-10}$ straight chain, branched or cyclic alkylthio or C$_{7-12}$ aralkylthio which may be substituted by 1 to 4 halogen atoms, (ii) pyrrolyl, imidazolyl, pyrazolyl, pyridyl, pyrimidyl, tetrazolyl, oxazolyl, isoxazolyl, oxadiazolyl, morpholino, thiazolyl, isothiazolyl, benzoxazolyl, benzofuryl or benzothienyl which may be substituted by 1 to 4 of the substituent groups (a) to (h) as listed in (i)

(iii) C$_1$ to C$_{10}$ straight-chain, branched or cyclic alkyl group which may be substituted by 1 to 4 halogen atoms, (iv) a halogen atom, (v) a hydroxyl, C$_{1-4}$ alkoxy, phenyl-C$_{1-4}$ alkyloxy which may be substituted by 1 to 4 halogen atoms, C$_{2-4}$ alkanoyloxy, or C$_{6-10}$ aryloxy groups which may be substituted by 1 to 4 halogen atoms, (vi) nitro, (vii) a C$_{1-10}$ alkylcarbonyl, or C$_{6-10}$ arylcarbonyl wherein the aryl group may be substituted by 1 to 4 of halogen atoms and C$_{1-4}$ alkoxy, (viii) acylamino wherein the acyl group is a C$_{1-10}$ alkylcarbonyl, or C$_{6-10}$ arylcarbonyl wherein the aryl group may be substituted by 1 to 4 of halogen atoms and C$_{1-4}$ alkoxy, (ix) an amino which may be substituted by 1 to 4 of C$_{1-10}$ alkyl, C$_{7-12}$ aralkyl and sulfonyl groups, (x) a C$_{1-10}$ straight-chain, branched or cyclic alkylthio group which may be substituted by 1 to 4 halogen atoms, and (xi) a C$_{7-12}$ aralkylthio which may be substituted by 1 to 4 halogen atoms, and R$^2$ is a group of the formula —COOR$^{2a}$ or —COSR$^{2a}$ wherein R$^{2a}$ is a C$_{1-10}$ alkyl or phenyl-C$_{1-4}$ aralkyl group which may be substituted by 1 to 3 of halogen and C$_{1-4}$ alkoxy, or its salt.

2. A compound according to claim 1, wherein the salt is a pharmaceutically acceptable salt.

3. A compound according to claim 1, wherein R$^1$ is a thiazolyl group which may be substituted by 1 to 2 of (i) a C$_{1-4}$ alkyl group and (ii) a C$_{6-10}$ aryl group which may be substituted by a C$_{3-6}$ cycloalkyl group or a phenyl- $C_{1-3}$ alkyloxy group which may be substituted by 1 to 4 halogen atoms.

4. A compound according to claim 1, wherein $R^2$ is a group of the formula —COOR$^{2a}$, wherein $R^{2a}$ is a $C_{1-10}$ alkyl, $C_{6-14}$ aryl or phenyl-$C_{1-4}$ alkyl group which may be substituted by 1 to 3 of halogen atoms and $C_{1-4}$ alkoxy.

5. A compound according to claim 4, wherein $R^{2a}$ is a $C_{1-4}$ alkyl or $C_{6-10}$ aryl group.

6. A compound according to claim 1, which is a compound of the formula

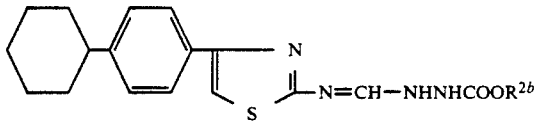

wherein $R^{2b}$ is a $C_{1-4}$ alkyl group or a $C_{6-10}$ aryl group, or a pharmaceutically acceptable salt thereof.

7. A compound according to claim 1, which is a compound of the formula

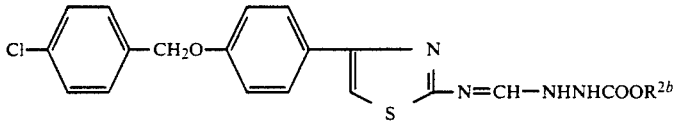

wherein $R^{2b}$ is a $C_{1-4}$ alkyl group or a $C_{6-10}$ aryl group, or a pharmaceutically acceptable salt thereof.

8. A compound according to claim 1, which is tert-butyl 3-[4-[4-(4-chlorobenzyloxy)phenyl]2-thiazolyl-iminomethyl]carbazate.

9. A compound according to claim 1, which is ethyl 3-[4-(4-cyclohexylphenyl)-2-thiazolyliminomethyl]-carbazate.

10. A carbazic acid derivative or its salt according to claim 1, wherein $R^1$ is a thiazolyl group which may be substituted by cyclohexylphenyl of chlorobenzyloxyphenyl.

11. An AGE-formation inhibitory agent which contains an effective amount of a carbazic acid derivative according to claim 1 or its pharmaceutically acceptable salt, together with a suitable carrier or carriers.

12. A method of inhibiting AGE-formation which comprises administering to a patient in need thereof an effective inhibitory dose of a compound

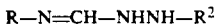

wherein R is (A) a 2-, 3- or 4-pyridyl, 2- or 3-thienyl, 2- or 3-furyl, 2-, 4- or 8-quinolyl, 1-, 4- or 8-isoquinolyl, 2-, 4- or 5-pyrimidinyl, 3- or 4-pyridazinyl, 2-, 4- or 5-thiazolyl, 2-, 4-or 5-imidazolyl, 4- or 5-isoxazolyl, 3-, 4- or 5-pyrazolyl, 2-, 4- or 5-imidazolyl, 4- or 5-(1,2,3-oxadiazolyl), 3- or 5-(1,2,4-oxadiazolyl), 1,3,4-oxadiazolyl, 1,2,5-oxadiazolyl, 3- or 5-(1,2,4-oxadiazolyl), 1,3,4-thiadiazolyl, benzimidazolyl, benzothiazolyl, tetrahydrobenzothiazolyl, quinazolyl, pteridinyl or benzoxazolyl group which may be substituted with 1 to 4 of the same or different substituents chosen from (i) a $C_{6-14}$ aryl which may be substituted by 1 to 4 of (a) $C_{1-10}$ straight-chain, branched or cyclic alkyl group which may be substituted by 1 to 4 halogen atoms,
(b) halogen,
(c) hydroxyl, $C_{1-4}$ alkoxy, phenyl-$C_{1-4}$ alkyloxy which may be substituted by 1 to 4 of halogen atoms, $C_{2-4}$ alkanoyloxy, or $C_{4-10}$ aryloxy which may be substituted by 1 to 4 halogen atoms,
(d) nitro,
(e) $C_{1-10}$ alkylcarbonyl, or $C_{6-10}$ arylcarbonyl wherein the aryl group may be substituted by 1 to 4 of halogen atoms or $C_{1-4}$ alkoxy,
(f) acylamino wherein the acyl group is a $C_{1-10}$ alkylcarbonyl, or $C_{6-10}$ arylcarbonyl wherein the aryl group may be substituted by 1 to 4 of halogen atoms or $C_{1-4}$ alkoxy,
(g) amino which may be substituted by 1 to 4 of $C_{1-10}$ alkyl, $C_{7-10}$ aralkyl and sulfonyl groups, or
(h) $C_{1-10}$ straight-chain, branched or cyclic alkylthio or $C_{7-12}$ aralkylthio which may be substituted by 1 to 4 halogen atoms, (ii) pyrrolyl, imidazolyl, pyrazolyl, pyridyl, pyrimidyl, tetrazolyl, oxazolyl, isoxazolyl, oxadiazolyl, morpholino, thiazolyl, isothiazolyl, benzoxazolyl, benzofuryl or benzothienyl which may be substituted by 1 to 4 of the substituent groups (a) to (h) as listed in (i)
(iii) $C_1$ to $C_{10}$ straight-chain, branched or cyclic alkyl group which may be substituted by 1 to 4 of halogen atoms,
(iv) a halogen atom,
(v) a hydroxyl, $C_{1-4}$ alkoxy, phenyl-$C_{1-4}$ alkyloxy which may be substituted by 1 to 4 of halogen atoms, $C_{2-4}$ alkanoyloxy, or $C_{6-10}$ aryloxy groups which may be substituted by 1 to 4 halogen atoms,
(vi) nitro,
(vii) a $C_{1-10}$ alkylcarbonyl, or $C_{6-10}$ arylcarbonyl wherein the aryl group may be substituted by 1 to 4 halogen atoms and $C_{1-4}$ alkoxy,
(viii) acylamino wherein the acyl group is a $C_{1-10}$ alkylcarbonyl, or $C_{6-10}$ arylcarbonyl wherein the aryl group may be substituted by 1 to 4 halogen atoms and $C_{1-4}$ alkoxy,
(ix) an amino which may be substituted by 1 to 4 of $C_{1-10}$ alkyl, $C_{7-12}$ aralkyl and sulfonyl group,
(x) a $C_{1-10}$ straight-chain, branched or cyclic alkylthio group which may be substituted by 1 to 4 halogen atoms, and
(xi) a $C_{7-12}$ aralkylthio which may be substituted by 1 to 4 halogen atoms, or (B) a $C_6$ to $C_{10}$ aryl group which may be substituted by 1 to 4 of the substituents (i) to (xi) as mentioned above in (A), and $R^2$ is a group of the formula —COOR$^{2a}$ or —COSR$^{2a}$ wherein $R^{2a}$ is a $C_1$ to $C_{10}$ alkyl, $C_6$ to $C_{14}$ aryl or phenyl-$C_{1-4}$ alkyl group which may be substituted by 1 to 3 of halogen and $C_1$ to $C_4$ alkoxy or its salt.

* * * * *